(12) United States Patent
Anderson et al.

(10) Patent No.: US 7,077,129 B2
(45) Date of Patent: Jul. 18, 2006

(54) DISPENSER WITH BIASED COVER

(75) Inventors: Gregor John McLennan Anderson, Ware (GB); Anthony James Taylor, Ware (GB)

(73) Assignee: Glaxo Group Limited, Greenford (GB)

( * ) Notice: Subject to any disclaimer, the term of this patent is extended or adjusted under 35 U.S.C. 154(b) by 141 days.

(21) Appl. No.: 10/168,751

(22) PCT Filed: Dec. 18, 2000

(86) PCT No.: PCT/EP00/12884

§ 371 (c)(1),
(2), (4) Date: Jun. 24, 2002

(87) PCT Pub. No.: WO01/47590

PCT Pub. Date: Jul. 5, 2001

(65) Prior Publication Data

US 2003/0010337 A1    Jan. 16, 2003

(30) Foreign Application Priority Data

Dec. 24, 1999  (GB) .................................. 9930602

(51) Int. Cl.
*A61M 15/00*   (2006.01)
*A61M 16/10*   (2006.01)
(52) U.S. Cl. ........................ 128/203.12; 128/203.15; 128/200.14
(58) Field of Classification Search ........... 128/200.14, 128/200.23, 208.12, 203.15
See application file for complete search history.

(56) References Cited

U.S. PATENT DOCUMENTS

| 4,749,351 | A | * | 6/1988 | Mahoney ..................... 431/252 |
| 4,949,875 | A |   | 8/1990 | Kuo |
| 5,408,994 | A | * | 4/1995 | Wass et al. ............ 128/203.15 |
| 5,482,030 | A | * | 1/1996 | Klein ..................... 128/200.23 |
| 5,482,187 | A |   | 1/1996 | Poulsen et al. |
| 5,547,091 | A | * | 8/1996 | Neveras et al. ............. 215/237 |
| 5,619,984 | A | * | 4/1997 | Hodson et al. ........ 128/203.15 |
| 5,921,237 | A | * | 7/1999 | Eisele et al. ........... 128/203.21 |
| 6,170,712 | B1 | * | 1/2001 | Kasboske ................... 222/215 |

FOREIGN PATENT DOCUMENTS

| EP | 0341967 A | 11/1989 |
| GB | 2161863 A | 1/1986 |
| WO | WO9925405 A | 5/1999 |

* cited by examiner

*Primary Examiner*—Glenn K. Dawson
*Assistant Examiner*—Michael Mendoza
(74) *Attorney, Agent, or Firm*—J. Michael Strickland

(57) ABSTRACT

There is provided a dispenser comprising a body for receipt of a carrier for a composition; an exit channel definable by the body for passage of the composition to a user; a cover for the exit channel reversibly movable between a storage position in which the cover fully protects the exit channel, to an in-use position wherein the exit channel is exposed. Biasing means act on the cover when the cover is not in the in-use or storage positions, to bias the cover towards either the in-use position or the storage position.

15 Claims, 7 Drawing Sheets

DISPENSER WITH BIASED COVER

This application is filed pursuant to 35 USC 371 as a U.S. National Phase Application of Ser. No. PCT/EP00/12884 filed Dec. 18, 2000, which claims priority from GB 9930602.9 filed Dec. 24, 1999 in the United Kingdom.

FIELD OF INVENTION

The present invention relates to a dispenser for dispensing the contents thereof. The invention relates particularly to a dispenser for the administration of medicament to a patient.

BACKGROUND TO THE INVENTION

It is well known to treat patients with medicaments contained in an aerosol, for example, in the treatment of respiratory disorders. It is also known to use for such treatment, medicaments which are contained in an aerosol and are administered to a patient by means of an inhalation device comprising a tubular housing or sleeve in which the aerosol container is located and an outlet tube leading out of the tubular housing. Such inhalation devices are generally referred to as metered dose inhalers (MDIs). The aerosol containers used in such inhalation devices are designed to deliver a predetermined dose of medicament upon each actuation by means of an outlet valve member at one end which can be opened either by depressing the valve member while the container is held stationary or by depressing the container while the valve member is held stationary. In the use of such devices, the aerosol container is placed in the tubular housing with the outlet valve member of the container communicating via a support with the outlet tube, for example a nozzle or mouthpiece. When used for dispensing medicaments, for example in bronchodilation therapy, the patient then holds the housing in a more or less upright condition and the mouthpiece or nozzle of the inhalation device is placed in the mouth or nose of the patient. The aerosol container is pressed towards the support to dispense a dose of medicament from the container which is then inhaled by the patient.

It is also known to use dry powder inhalation devices for the delivery of inhalable medicament. In one aspect, such dispensers comprise pre-metered doses of powdered medicament, for example in capsules or blisters. In another aspect, such dispensers comprise a reservoir of powdered medicament from which doses are metered prior to or concurrent with the delivery process. In either case, the device may be designed for passive release of medicament, where the medicament is simply made available at a delivery position for aerosolisation in response to the inhalation of the patient. Alternatively, an active release mechanism may be used whereby a 'puff' of compressed gas or air is provided to the delivery position to assist in aerosolisation of the powder prior to or concurrent with the inhalation of the patient. Such devices are generally called active release dry powder inhalers (active DPIs). The source of the compressed gas or air is generally an aerosol container.

It is also well known to use syringes for the delivery of injectable medicament to a patient. Traditional syringes rely on puncturing of the patient's skin by a hollow needle through which the injectable medicament (in solution or suspension form) is delivered to the muscle or tissue of the patient. Recently developed needleless systems for the delivery of injectables employ high velocity injection of particle formulated drugs or vaccine through the skin and into any physically accessible tissue. Other needleless systems employ similar high velocity injection of drug or vaccine coated on to a suitable carrier particle.

Other forms of medicament dispenser, such as bottles, tubes or vials, are known in the art, which comprise an exit channel (or nozzle) for dispensing medicament therefrom. In a typical dispensing operation using any of the above devices, the body of the device is held by the patient and the exit channel (or nozzle) of the device is placed in the mouth/nose or on the skin, or in the palm of the patient's hand.

When not in use it is desirable, from a hygiene standpoint, that the exit channel is provided with some kind of protective cover. The cover desirably acts both to prevent build-up of dirt on the exit channel and to prevent ingress of dirt into the body of the device through the channel, which might then be subject to administration by a patient. It is desirable for the cover to be joined to the body of the device so that it cannot be separated from the device.

Patient trials of various medicament dispensers have shown that patients do not always fully expose the exit channel before attempting to use the device or fail to fully protect it when the device is not in use.

The applicants have now found that this problem can be overcome by the use of a cover which has biasing means acting upon it. The biasing means enables the cover to move in a reversible manner directly from the in-use position, when the exit channel is fully exposed, to the storage position, wherein the exit channel is fully protected by the cover.

A further advantage of the present invention is that the exit channel cover is provided with a clear portion to enable viewing of the exit channel when the exit channel is fully protected. This clear portion also enables viewing of a dose counter or alphanumeric display when the exit channel is fully exposed.

The Applicants have also found that the present invention has utility in protecting the exit channel of a wide range of dispensers, including food and toiletry dispensers.

SUMMARY OF THE INVENTION

According to one aspect of the present invention there is provided a dispenser comprising a body for receipt of a carrier for a composition; an exit channel definable by the body for passage of the composition to a user; a cover for the exit channel reversibly movable between a storage position in which the cover fully protects the exit channel, to an in-use position wherein the exit channel is exposed; and biasing means acting on the cover when the cover is not in said in-use or storage positions, to bias the cover towards either the in-use position or the storage position.

In one aspect, the dispenser additionally comprises a control element to control the amount of biasing energy acting on the cover.

Preferably the control element defines a biasing energy curve varying according to the proximity of the cover to the storage and in-use positions. Preferably the biasing energy curve reaches a maximum when the cover is at a definite point between the starting and in-use positions. More preferably, the biasing energy curve has a single maximum.

In one aspect, the biasing energy curve is symmetrical.

In another aspect, the biasing energy curve is asymmetrical.

In a further aspect, the control element comprises a cam surface and a cam follower.

In one aspect, the control element comprises a ramp.

In another aspect, the biasing means comprises a spring.

In a further aspect, the biasing means comprises an articulated assembly.

Preferably, the biasing means comprises resilient material.

In one aspect, the biasing means comprises a pressure based system. Preferably, the pressure based system is a pneumatic system. More preferably, the pressure based system is a hydraulic system.

In another aspect, the cover is reversibly lockable in the storage or in-use positions.

In one aspect, the cover is rotatably movable. Preferably, the cover is slidably movable.

In a further aspect, the biasing means comprises a spring, and the control element comprises a cam surface and cam follower.

In another aspect, the biasing means comprises an articulated assembly and the control element comprises a ramp.

In one aspect, the biasing means comprises a resilient plug movable between two sockets and the control element comprises the surface between the two sockets.

In another aspect, the cover is movable by a sliding thumb motion. Preferably the cover is movable by one-handed operation. More preferably, the cover is movable by a right-handed or left-handed user.

In one aspect, the dispenser additionally comprises a carrier. Preferably the carrier is selected from the group consisting of aerosol container, tube, bottle, phial, vial, blister strip and capsule.

In another aspect, the carrier additionally comprises a composition.

Preferably, the physical form of the medicament is selected from the group consisting of cream, ointment, powder, solution, suspension, tablet and emulsion.

Preferably, the carrier is an aerosol container.

More preferably, the aerosol container additionally comprises a suspension of a composition in a propellant. More preferably, the propellant comprises liquefied HFA134a, HFA-227 or carbon dioxide.

In another aspect, the carrier is a dry-powder container.

Preferably, the dry-powder container comprises a composition and optionally excipient in dry-powder form.

Optionally, the medicament carrier is a liquid container. Preferably, the liquid container comprises a solution of composition in a solvent.

In one aspect, the composition comprises a medicament.

Preferably, the medicament is selected from the group consisting of albuterol, salmeterol, fluticasone propionate and beclomethasone dipropionate and salts or solvates thereof and any mixtures thereof.

In another aspect, the cover has a clear portion to enable the user to see the location of the exit channel when in the storage position.

In a further aspect, the dispenser is additionally provided with a dose counter display.

Preferably, the dose counter display is visible through the clear portion of the cover when the cover is in the in-use position.

Preferably, the dispenser is additionally provided with an alphanumeric display. More preferably, the alphanumeric display is visible through the clear portion of the cover when the cover is in the in-use position.

In one aspect, the composition comprises a foodstuff. Preferably, the foodstuff is selected from the group consisting of tomato puree, mustard, fish paste, meat paste, sweet sauce, savoury sauce and pate.

In another aspect, the composition comprises a toiletry. Preferably, the toiletry is selected from the group consisting of toothpaste, deodorant, soap, eye drop, shampoo, moisturising cream and hand cream.

In another aspect of the present invention, there is provided the use of dispenser according to the present invention for dispensing medicament.

In a further aspect of the present invention there is provided a kit of parts comprising a dispenser according to the present invention and a medicament carrier.

BRIEF DESCRIPTION OF THE DRAWINGS

The invention will now be described with reference to the accompanying drawings in which:

FIG. 4c shows a sectional view of the biasing means and control element of FIG. 3 when the cover is in the opposite position to that of FIG. 4a.

DETAILED DESCRIPTION OF THE DRAWINGS

Figure 1A:
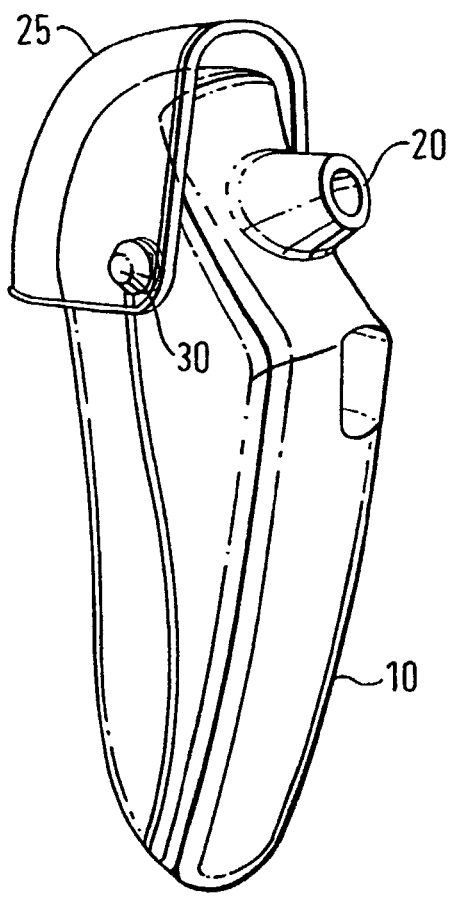
FIG. 1a shows a perspective view of medicament dispenser in accord with the present invention with the cover in the in-use position.
Figure 1B:
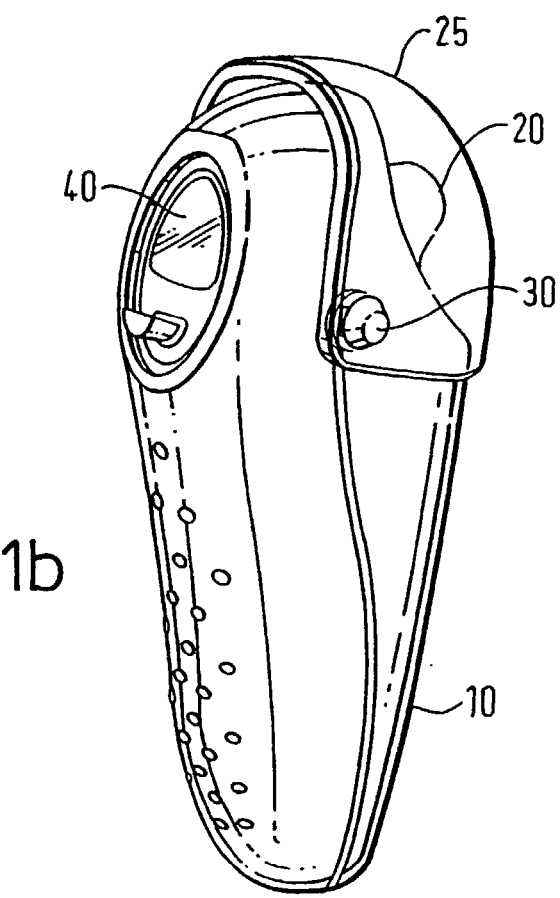
FIG. 1b shows a perspective view of an medicament dispenser in accord with the present invention with the cover in the storage position.

FIGS. 1a and 1b show a medicament dispenser according to the present invention comprising a body 10, an exit channel or mouthpiece 20, an exit channel or mouthpiece cover 25 and pivoting means 30 to connect the cover 25 to the body 10 and to pivot the cover 25 with respect to the body 10. The pivoting means 30 are also involved in the biasing mechanism and may be directly or indirectly connected to the biasing means and control element or may consist of a shaft connecting to both sides of the cover and containing the biasing means and control element.

A display 40 may be additionally present on the device and can be used to indicate the number of doses remaining in or dispensed from a medicament carrier (hidden) contained within the body 10. The mouthpiece cover 25 can be made from a clear material to enable the user of the device to see the display 40 when the cover 25 is in the in-use position (FIG. 1a) and to see the location of the mouthpiece 20 when the cover 25 is in the storage position (FIG. 1b).

The device is shaped so that one-handed operation is facilitated whereby the palm and fingers of one hand can grip the device and the cover 25 is movable by a motion of the thumb of the same hand. One-handed operation of the device is possible by either a right-handed or left-handed user.

Figure 2A:
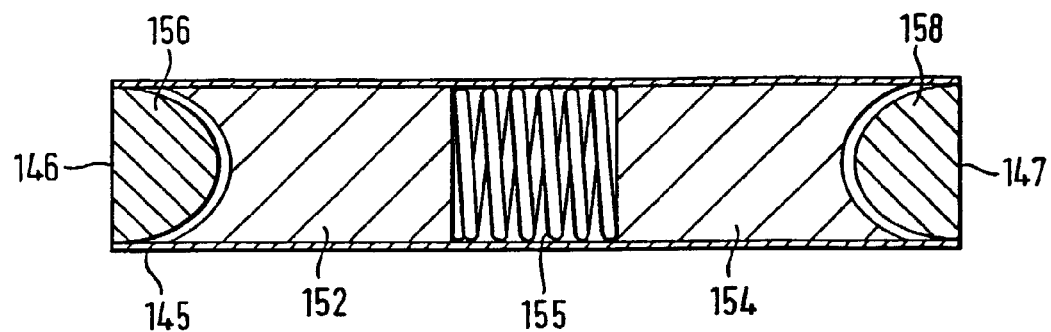
FIG. 2a shows a sectional view through a shaft containing a first biasing means and control element suitable for the device of FIGS. 1a and 1b, but not exclusive thereto, when the cover is in the storage or in-use positions.
Figure 2B:
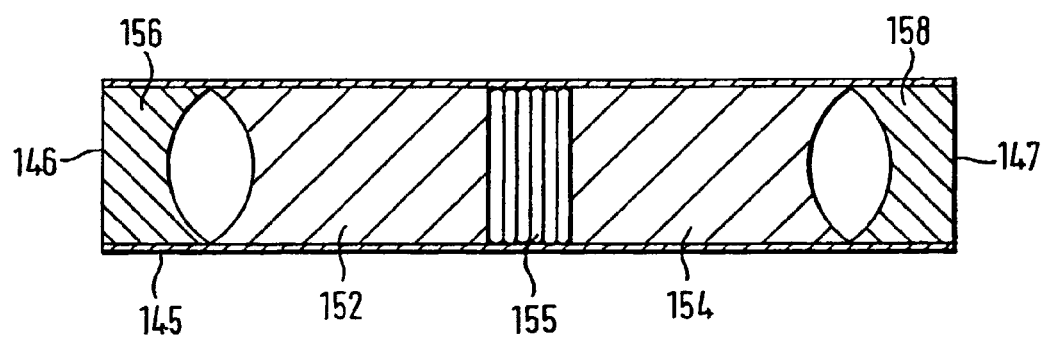
FIG. 2b is a sectional view through a shaft containing a first biasing means and control element suitable for the device of FIGS. 1a and 1b, but not exclusive thereto, when the cover is moving between the storage and in-use positions and at the position of maximum biasing energy.

FIGS. 2a and 2b show a biasing mechanism contained within a shaft 145. The ends 146, 147 of the shaft 145 are connectable to the pivoting means shown in FIGS. 1a and 1b. Located in, but not fixed to, the shaft are two cams 152, 154 separated by a spring 155. Fixed to each end 146, 147 of the shaft 145 are cam followers 156, 158.

When the cover is in the storage or in-use position, the spring 155 is relaxed and the cams 152, 154 and cam followers 156, 158 are positioned as shown in FIG. 2a. The cam followers 156, 158 are shaped so that in one position they have a shape complementary to that of the ends of the cams 152, 154 and when rotated have a shape which is non-complementary to that of the ends of the cams 152, 154. As the cam followers 156, 158 are rotated, due to movement of the cover, the cams 152, 154 are pushed together by the cam followers 156, 158 and this movement compresses the spring 155, increasing the biasing energy available. The biasing energy curve defined by movement of the cam followers 156, 158 relative to the cams 152, 154 is symmetrical. Alternatively the cam may define an asymmetrical profile wherein the biasing curve is engineered to favour either the in-use position or the storage position.

Movement of the cam followers 156, 158 by an angle of less than 90° relative to the cams 152, 154 results in movement of the cam followers 156, 158 (and hence the shaft and cover) back to their starting position. The amount of biasing energy available increases with the angle of movement of the cam followers 156, 158, due to increased compression of the spring 155, so that maximum biasing energy is available when the cam followers 156, 158 have moved exactly 90° relative to the cams 152, 154. This arrangement of the cams 152, 154 and cam followers is shown in FIG. 2b.

Movement of the cam followers 156, 158 by an angle greater than 90° results in continued movement of the cam followers 156, 158 through a further 90° until the spring 155 is relaxed and the biasing energy available is back to zero. This 180° movement results in switching of the cover from the storage position to the in-use position or vice versa.

Figure 3:
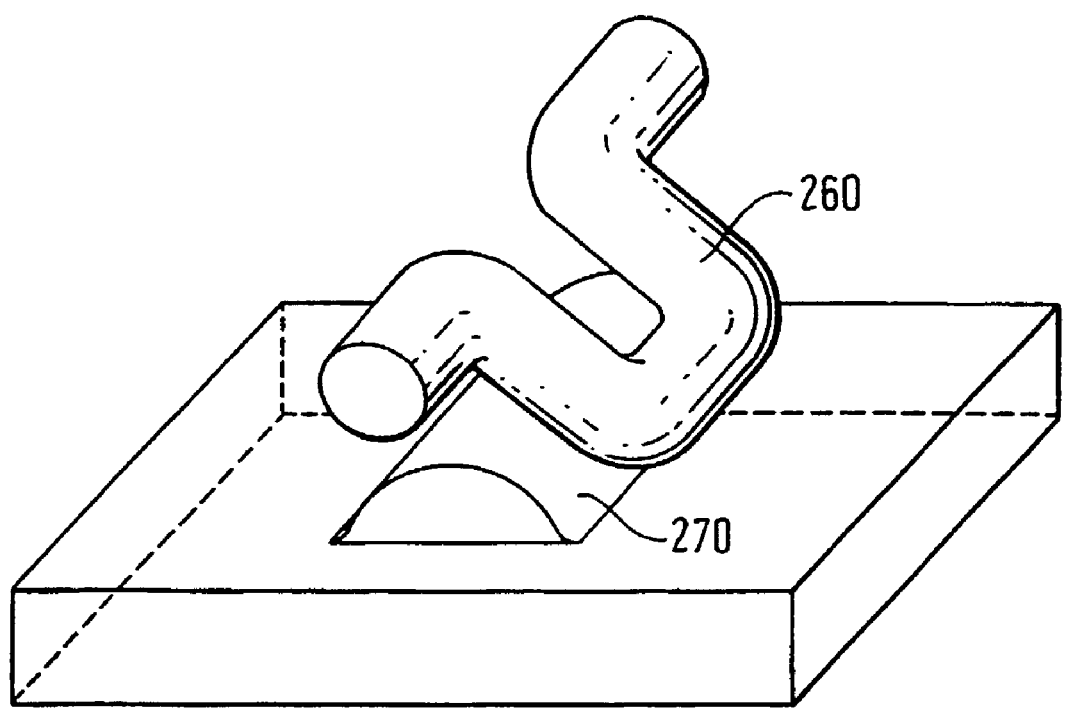
FIG. 3 shows a perspective view of a second biasing means and control element suitable for the device of FIGS. 1a and 1b, but not exclusive thereto.

FIG. 3 shows a biasing mechanism comprising an articulated assembly 260 and a ramp 270. The articulated assembly 260 is connectable with the pivoting means shown in FIGS. 1a and 1b so that movement of the cover results in movement of the articulated assembly 260. The ramp 270 is fixed to an internal portion of the body of the medicament dispenser.

Figure 4A:
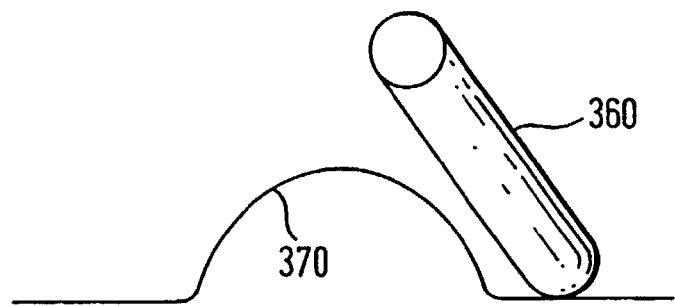
FIG. 4a shows a sectional view of the biasing means and control element of FIG. 3 when the cover is in the in-use or storage positions.
Figure 4B:
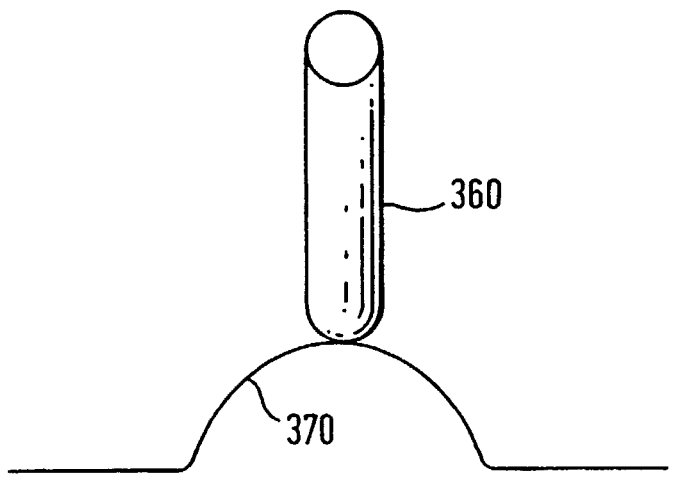
FIG. 4b shows a sectional view of the biasing means and control element of FIG. 3 when the cover is moving between the in-use or storage positions.
Figure 4C:
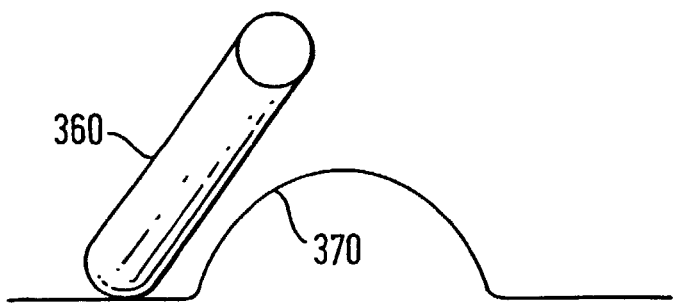

The movement of the articulated assembly is shown by a sectional view in FIGS. 4a, 4b and 4c. When the cover is in the in-use and storage positions the articulated assembly 360 is located at the bottom of the ramp 370 and the biasing energy is zero (FIG. 4a). Movement of the cover results in movement of the articulated assembly 360 up the ramp 370. If the articulated assembly 360 is moved partially up one side of the ramp 370 then the articulated assembly 360 will move back down the ramp 370 to its starting position which has the minimum level of biasing energy. The position of maximum biasing energy is reached when the articulated assembly 360 reaches the highest point of the ramp 370 (FIG. 4b). When the articulated assembly 360 passes this point then the cover is biased towards the other position (FIG. 4c).

Figure 5A:
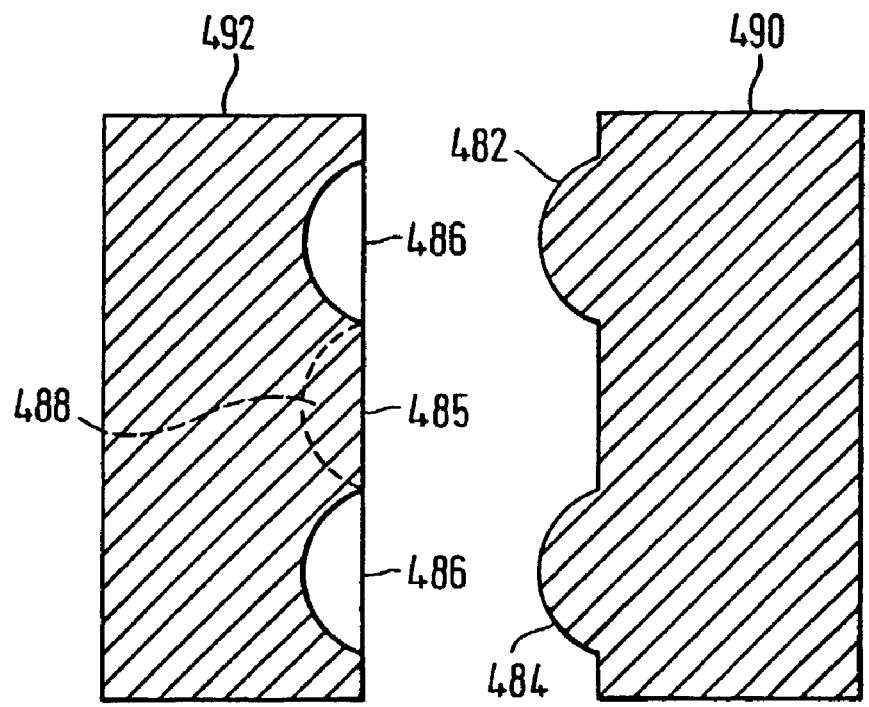
FIG. 5a shows a sectional view of a third biasing means and control element suitable for the device of FIGS. 1a and 1b, but not exclusive thereto.
Figure 5B:
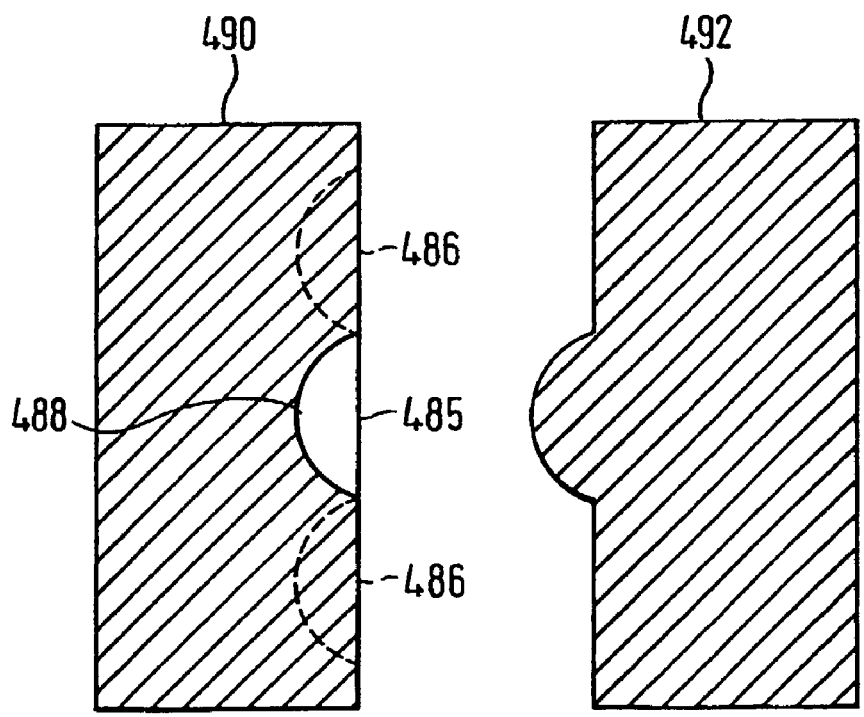
FIG. 5b shows a sectional view of the third biasing means and control element of FIG. 5a, rotated through 90°.

A sectional view of a plug and socket biasing mechanism is shown in FIGS. 5a and 5b. FIG. 5a shows two segments 490, 492, one of which contains two double sets of sockets 486, 488 and the other which has the plugs 482, 484. When the cover is in the storage or in-use position, the plugs 482, 484 occupy one set of the sockets 486. The plugs 482, 484 are composed of resilient material so that when the cover is moved, the plugs 482, 484 are pushed out of one set of sockets 486 and along the surface 485 between the two sets of sockets 486, 488 until they reach the next set of sockets 488 as shown in FIG. 5b. The maximum level of biasing energy is reached at the mid point of the surface 485 between the sets of sockets 486, 488. When the plugs 482, 484 pass through this point then they will move to the other set of sockets 488; however if the plugs 482, 484 only move part of the way towards this mid point then they will be biased to return to their starting position. The distance between the sets of sockets 486, 488 defines the amount of biasing.

Figure 6:
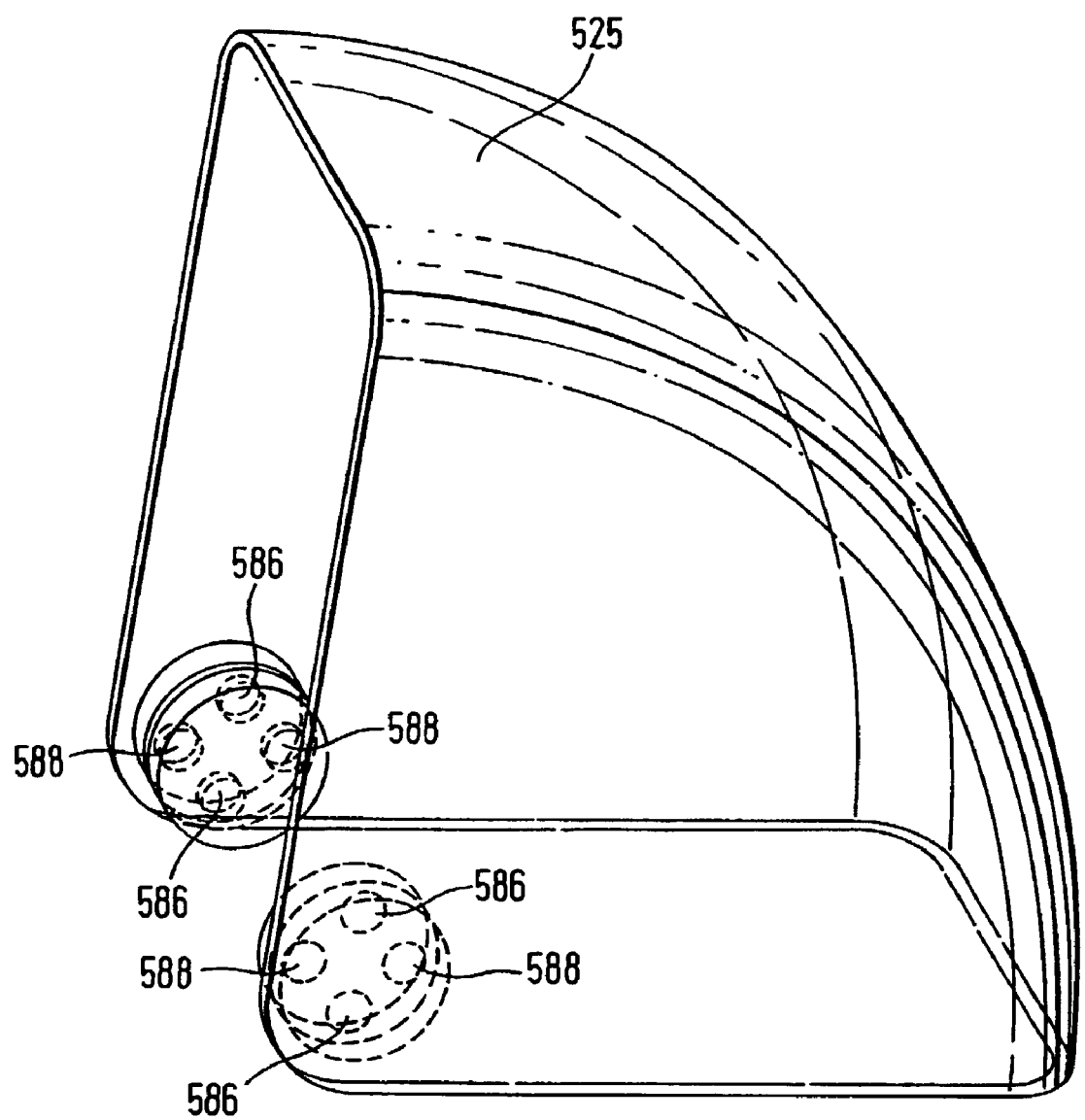
FIG. 6 shows a perspective view of the cover of FIGS. 1a and 1b showing the location of the biasing means and control element of FIGS. 5a and 5b.

FIG. 6 shows the location of the sockets of FIGS. 5a and 5b on the cover 525 of the device of FIGS. 1a and 1b. The biasing mechanism (not shown) is directly involved in the pivoting of the cover 525. Each side of the cover has two sets of double sockets 586, 588, arranged as shown in FIG. 6 and these sets of sockets define the two positions of the cover 525: the storage and in-use positions.

Figure 7A:
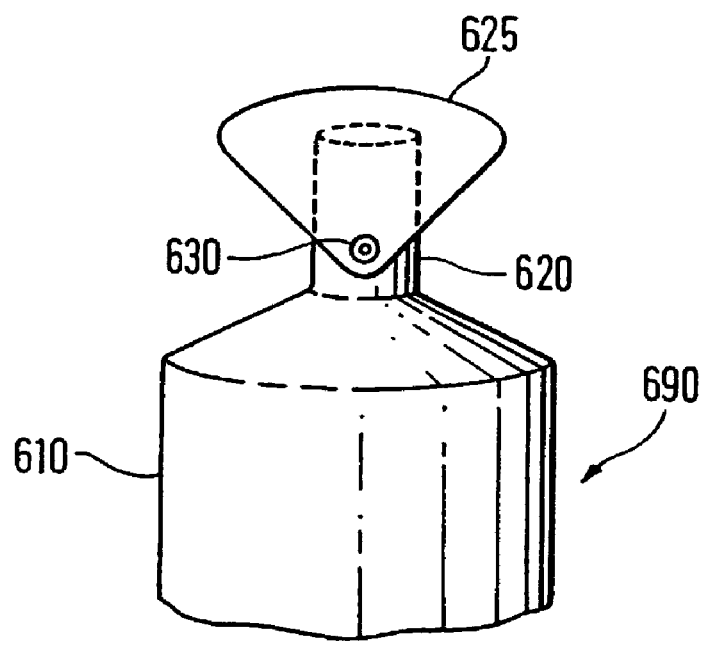
FIG. 7a shows a perspective view of a medicament dispenser in accord with the present invention with the cover in the storage position.
Figure 7B:
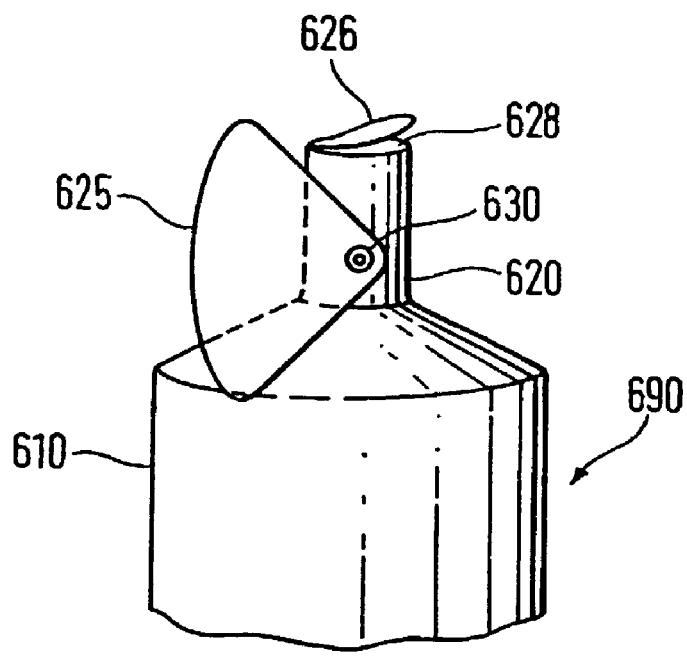
FIG. 7b shows a perspective view of a medicament dispenser in accord with the present invention with the cover in the in-use position.

FIGS. 7a and 7b show a medicament dispenser, in the form of tube 690, for dispensing medicament according to the present invention. The tube 690 comprises a body 610, exit channel or nozzle 620, cover 625 and pivoting means 630 to connect the cover 625 to the nozzle 620. It will also be understood that in another embodiment of the invention, the cover 625 may be connected to the body 610 by pivoting means 630. The cover 625 is free to pivot with respect to the body 610. The pivoting means 630 are also involved in the biasing mechanism and may be directly or indirectly connected to the biasing means and control element or may consist of a shaft connecting to both sides of the cover and containing the biasing means and control element.

In FIG. 7a the tube 690 is in the storage-position, with the cover 625 protecting exit channel or nozzle 620. A lid 626, which may be composed of aluminium foil or a suitable plastic, seals the orifice 628 of nozzle 620. Cover 625 is movable, by a motion of the thumb of the user's hand holding tube 690, to the in-use position (FIG. 7b) thereby exposing lid 626 which may be peeled from orifice 628. Medicament may be dispensed from tube 690 by squeezing body 610 in the palm of the user's hand, thereby forcing medicament in the form of ointment or cream from nozzle 620. Cover 625 is returned to the storage position (FIG. 7a) by the action of the user's thumb of the hand gripping the tube 690. One-handed operation of the medicament container or tube is therefore possible by either a right-handed or left-handed user.

It may be appreciated that any of the parts of the dispenser which contact the medicament may be coated with materials such as fluoropolymer materials which reduce the tendency of medicament to adhere thereto. Any movable parts may also have coatings applied thereto which enhance their desired movement characteristics. Frictional coatings may therefore be applied to enhance frictional contact and lubricants used to reduce frictional contact as necessary.

The medicament dispenser of the invention is suitable for dispensing medicament, particularly for the treatment of respiratory disorders such as asthma and chronic obstructive pulmonary disease. Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. as the sodium salt), ketotifen or nedocromil (e.g. as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α, 9α-difluoro-11β-hydroxy-16α-methyl-3-oxo-17α-propionyloxy-androsta-1,4-diene-17β-carbothioic acid S-(2-oxo-tetrahydro-furan-3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, e.g. 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3, 4-diol (e.g. as maleate); α4 integrin inhibitors e.g. (2S)-3-[4-({[4-(aminocarbonyl)-1-piperidinyl]carbonyl}oxy) phenyl]-2-[((2S)-4-methyl-2-{[2-(2-methylphenoxy)acetyl] amino}pentanoyl)amino] propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant. Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) or formoterol (e.g. as the fumarate salt) in combination with an antiinflammatory steroid such as a beclomethasone ester (e.g., the dipropionate) or a fluticasone ester (e.g., the propionate) or budesonide. A particularly preferred combination is a combination of fluticasone propionate and salmeterol, or a salt thereof (particularly the xinafoate salt). A further combination of particular interest is budesonide and formoterol (e.g. as the fumarate salt).

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

What is claimed is:

1. A dispenser comprising:
    a body for receipt of a carrier for a composition;
    an exit channel definable by said body for passage of said composition to a user;
    a cover for said exit channel reversibly movable between a storage in which said cover fully protects the exit channel, to an in-use position wherein the exit channel is exposed;
    a biasing element capable of generating a biasing energy for acting on the cover when the cover is not in said in-use or storage positions, capable of biasing the cover towards either the in-use position or the storage position depending on the location of the cover between its storage and in-use positions; and
    a control element cooperatively engaging the biasing element to control the direction of the bias acting on the cover,
wherein said control element defines a biasing energy curve varying according to the proximity of the cover to the storage and in-use positions, and wherein the biasing energy curve has a maximum when the cover is at a defined point between the storage and the in-use position such as to bias the cover away from said defined point and towards either the in-use position or the storage position, and wherein the control element comprises a cam surface and a cam follower.

2. A dispenser comprising
    a body for receipt of a carrier for a composition; an exit channel definable by said body for passage of said composition to a user;
    a cover for said exit channel reversibly movable between a storage position in which said cover fully protects the exit channel, to an in-use position wherein the exit channel is exposed;
    a biasing element capable of generating a biasing energy for acting on the cover when the cover is not in said in-use or storage positions, capable of biasing the cover towards either the in-use position or the storage position depending on the location of the cover between its storage and in-use positions; and
    a control element cooperatively engaging the biasing element to control the direction of the bias acting on the cover,
wherein said control element defines a biasing energy curve varying according to the proximity of the cover to the storage and in-use positions, and wherein the biasing energy curve has a maximum when the cover is at a defined point between the storage and the in-use position such as to bias the cover away from said defined point and towards either the in-use position or the storage position, and wherein the control element comprises a ramp.

3. A dispenser comprising
    a body for receipt of a carrier for a composition;
    an exit channel definable by said body for passage of said composition to a user;
    a cover for said exit channel reversibly movable between a storage position in which said cover fully protects the exit channel, to an in-use position wherein the exit channel is exposed;

a biasing element capable of generating a biasing energy for acting on the cover when the cover is not said in-use or storage positions, capable of biasing the cover towards either the in-use position or the storage position depending on the location of the cover between its storage and in-use positions; and a control element cooperatively engaging the biasing element to control the direction of the bias acting on the cover, wherein said control element defines a biasing energy curve varying according to the proximity of the cover to the storage and in-use positions, and wherein the biasing energy curve has a maximum when the cover is at a defined point between the storage and the in-use position such as to bias the cover away from said defined point and towards either the in-use position or the storage position, wherein the biasing element comprises a pressure based system, and wherein the pressure based system is a pneumatic system.

4. A dispenser comprising
a body for receipt of a carrier for a composition;
an exit channel definable by said body for passage of said composition to a user;
a cover for said exit channel reversibly movable between a storage position in which said cover fully protects the exit channel, to an in-use position wherein the exit channel is exposed;
a biasing element capable of generating a biasing energy for acting on the cover when the cover is not in said in-use or storage positions, capable of biasing the cover towards either the in-use position or the storage position depending on the location of the cover between its storage and in-use positions; and
a control element cooperatively engaging the biasing element to control the direction of the bias acting on the cover,
wherein said control element defines a biasing energy curve varying according to the proximity of the cover to the storage and in-use positions, and wherein the biasing energy curve has a maximum when the cover is at a defined point between the storage and the in-use position such as to bias the cover away from said defined point and towards either the in-use position or the storage position, wherein the biasing element comprises a pressure based system, and wherein the pressure based system is a hydraulic system.

5. A dispenser comprising
a body for receipt of a carrier for a composition;
an exit channel definable by said body for passage of said composition to a user;
a cover for said exit channel reversibly movable between a storage position in which said cover fully protects the exit channel, to an in-use position wherein the exit channel is exposed;
a biasing element capable of generating a biasing energy for acting on the cover when the cover is not in said in-use or storage positions, capable of biasing the cover towards either the in-use position or the storage position depending on the location of the cover between its storage and in-use positions; and
a control element cooperatively engaging the biasing element to control the direction of the bias acting on the cover,
wherein said control element defines a biasing energy curve varying according to the proximity of the cover to the storage and in-use positions, and wherein the biasing energy curve has a maximum when the cover is at a defined point between the storage and the in-use position such as to bias the cover away from said defined point and towards either the in-use position or the storage position, and wherein the cover is slidably movable.

6. A dispenser comprising
a body for receipt of a carrier for a composition;
an exit channel definable by said body for passage of said composition to a user;
a cover for said exit channel reversibly movable between a storage position in which said cover fully protects the exit channel, to an in-use position wherein the exit channel is exposed;
a biasing element capable of generating a biasing energy for acting on the cover when the cover is not in said in-use or storage positions, capable of biasing the cover towards either the in-use position or the storage position depending on the location of the cover between its storage and in-use positions; and
a control element cooperatively engaging the biasing element to control the direction of the bias acting on the cover,
wherein said control element defines a biasing energy curve varying according to the proximity of the cover to the storage and in-use positions, and wherein the biasing energy curve has a maximum when the cover is at a defined point between the storage and the in-use position such as to bias the cover away from said defined point and towards either the in-use position or the storage position, and wherein the biasing element comprises a spring, and the control element comprises a cam surface and cam follower.

7. A dispenser comprising
a body for receipt of a carrier for a composition;
an exit channel definable by said body for passage of said composition to a user;
a cover for said exit channel reversibly movable between a storage position in the exit channel is exposed;
a biasing element capable of generating a biasing energy for acting on the cover when the cover is not in said in-use or storage positions, capable of biasing the cover towards either the in-use position or the storage position depending on the location of the cover between its storage and in-use positions; and
a control element cooperatively engaging the biasing element to control the direction of the bias acting on the cover,
wherein said control element defines a biasing energy curve varying according to the proximity of the cover to the storage and in-use positions, and wherein the biasing energy curve has a maximum when the cover is at a defined point between the storage and the in-use position such as to bias the cover away from said defined point and towards either the in-use position or the storage position, and wherein the biasing element comprises an articulated assembly and the control element comprises a ramp.

8. A dispenser comprising
a body for receipt of a carrier for a composition;
an exit channel definable by said body for passage of said composition to a user;
a cover for said exit channel reversibly movable between a storage position in which said cover fully protects the exit channel, to an in-use position wherein the exit channel is exposed;
a biasing element capable of generating a biasing energy for acting on the cover when the cover is not in said in-use or storage positions, capable of biasing the cover towards either the in-use position or the storage position depending on the location of the cover between its storage and in-use positions; and a control element cooperatively engaging the biasing element to control the direction of the bias acting on the cover, wherein said control element defines a biasing energy curve varying according to the proximity of the cover to the storage and in-use positions, and wherein the biasing energy curve has a maximum when the cover is at a defined point between the storage and the in-use position such as to bias the cover away from said defined point and towards either the in-use position or the storage position, and wherein the cover is movable by sliding thumb motion.

9. A dispenser comprising
a body for receipt of a carrier for a composition;
an exit channel definable by said body for passage of said composition to a user;
a cover for said exit channel reversibly movable between a storage position in which said cover fully protects the exit channel, to an in-use position wherein the exit channel is exposed;
a biasing element capable of generating a biasing energy for acting on the cover when the cover is not in said in-use or storage positions, capable of biasing the cover towards either the in-use position or the storage position depending on the location of the cover between its storage and in-use positions; and
a control element cooperatively engaging the biasing element to control the direction of the bias acting on the cover, wherein said control element defines a biasing energy curve varying according to the proximity of the cover to the storage and in-use positions, and wherein the biasing energy curve has a maximum when the cover is at a defined point between the storage and the in-use position such as to bias the cover away from said defined point and towards either the in-use position or the storage position, and wherein the cover has a clear portion to enable the user to see the location of the exit channel when in the storage position.

10. A dispenser comprising
a body for receipt of a carrier for a composition;
an exit channel definable by said body for passage of said composition to a user;
a cover for said exit channel reversibly movable between a storage position in which said cover fully protects the exit channel, to an in-use position wherein the exit channel is exposed;
a biasing element capable of generating a biasing energy for acting on the cover when the cover is not in said in-use or storage positions, capable of biasing the cover towards either the in-use position or the storage position depending on the location of the cover between its storage and in-use positions; and
a control element cooperatively engaging the biasing element to control the direction of the bias acting on the cover, wherein said control element defines a biasing energy curve varying according to the proximity of the cover to the storage and in-use positions, and wherein the biasing energy curve has a maximum when the cover is at a defined point between the storage and the in-use position such as to bias the cover away from said defined point and towards either the in-use position or the storage position, and wherein the dispenser is additionally provided with a dose counter display.

11. A dispenser according to claim 10, wherein said dose counter display is visible through the clear portion of the cover when the cover is in the in-use position.

12. A dispenser comprising
a body for receipt of a carrier for a composition;
an exit channel definable by said body passage of said composition to a user;
a cover for said exit channel reversibly movable between a storage position in which said cover fully protects the exit channel, to an in-use position wherein the exit channel is exposed;
a biasing element capable of generating a biasing energy for acting on the cover when the cover is not in said in-use or storage positions, capable of biasing the cover towards either the in-use position or the storage position depending on the location of the cover between its storage and in-use positions; and
a control element cooperatively engaging the biasing element to control the direction of the bias acting on the cover, wherein said control element defines a biasing energy curve varying according to the proximity of the cover to the storage and in-use positions, and wherein the biasing energy curve has a maximum when the cover is at a defined point between the storage and the in-use position such as to bias the cover away from said defined point and towards either the in-use position or the storage position, and wherein the dispenser is additionally provided with an alphanumeric display.

13. A dispenser according to claim 12, wherein the alphanumeric display is visible through the clear portion of the cover when the cover is in the in-use position.

14. A dispenser comprising:
(a) a body in receipt of a carrier for a composition, said body defining an exit channel for passage of said composition to a user;
(b) a cover for said exit channel, said cover defining opposing interior surfaces;
(c) at least one inwardly directed cam follower about which said cover pivots, said cam follower defined by or connected to said interior surface, said cam follower having a cam follower face;
(d) a hollow shaft associated with said body, said hollow shaft at least partially enclosing a spring, at least one cam and said cam follower face, said spring communicating with said cam and said cam defining a mating face which abuts said cam follower face;

wherein said cover is reversibly and pivotally movable between a storage position, in which said cover fully protects the exit channel, to an in-use position, wherein the exit channel is exposed; and wherein movement of said cover rotates said cam follower face causing partial distancing of the cam follower and cam mating face and compression of said spring to create a biasing force biasing said cover toward either the storage position or in use position, depending on the degree of rotation of the cover.

15. The dispenser of claim 14, wherein said mating face of said cam further comprises a surface defining a peak and a trough, and said cam follower face has a surface defining a corresponding peak and trough, and wherein the peak of one surface resides in the trough of the other surface when said cover is the in-use position or in the storage position, and the distance between the mating face and the cam follower face is at a minimum.

* * * * *